(12) United States Patent
Kuno et al.

(10) Patent No.: US 7,737,268 B2
(45) Date of Patent: Jun. 15, 2010

(54) METHOD OF RECOVERING NUCLEIC ACIDS AND KIT FOR RECOVERING NUCLEIC ACIDS

(75) Inventors: Norihito Kuno, Tsurugashima (JP); Kenko Uchida, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 850 days.

(21) Appl. No.: 10/848,368

(22) Filed: May 19, 2004

(65) Prior Publication Data

US 2004/0235034 A1 Nov. 25, 2004

(30) Foreign Application Priority Data

May 19, 2003 (JP) ............................. 2003-139751

(51) Int. Cl.
*C07H 21/00* (2006.01)
*C12Q 1/68* (2006.01)
*C12P 19/34* (2006.01)

(52) U.S. Cl. ........................ 536/25.4; 435/6; 435/91.2

(58) Field of Classification Search ....................... None
See application file for complete search history.

(56) References Cited

U.S. PATENT DOCUMENTS

| | | | |
|---|---|---|---|
| 5,155,018 | A | 10/1992 | Gillespie et al. |
| 6,613,895 | B1 * | 9/2003 | Gautsch et al. ............ 536/25.4 |
| 2003/0138828 | A1 * | 7/2003 | Bost et al. ...................... 435/6 |
| 2004/0175735 | A1 * | 9/2004 | Sakurai et al. ................. 435/6 |

FOREIGN PATENT DOCUMENTS

| | | |
|---|---|---|
| JP | 9-508638 | 2/1995 |
| JP | 2002-187897 | 2/1995 |
| JP | 10-155481 | 6/1997 |
| JP | 11-196869 | 1/1998 |
| WO | WO 95/21849 | 2/1995 |
| WO | WO 97/30062 | 2/1997 |
| WO | WO 97/30152 | 2/1997 |

OTHER PUBLICATIONS

Fiore et al., 2000, J of Micobiol. Methods 39: 159-169.*
Kitos PA et al 'Adsorption of polyadenylate and other polynucleotides to unmodified cellulose.' Biochemistry. Dec. 4, 1973;12(25):5086-91.*
Beld M et al 'Fractionation of nucleic acids into single-stranded and double-stranded forms.' Nucleic Acids Res. Jul. 1, 1996;24(13):2618-9.*
Herzer S 'DNA Purification' (2002) in Molecular Biology Problem Solver, pp. 167-195.*
Bavykin, Sergei G., et al.; "Portable System for Microbial Sample Preparation and Oligonucleotide Microarray Analysis", Applied and Environmental Microbiology, Feb. 2001, vol. 67, No. 2, pp. 922-928.
Uyttendaele, M., et al.; "Influence of bacterial age and pH of lysis buffer on type of nucleic acid isolated", Journal of Microbiological Methods, vol. 26, 1996, pp. 133-138.
Boom, R., et al., "Rapid and Simple Method for Purification of Nucleic Acids", Journal of Clinical Microbiology, Mar. 1990, vol. 28, No. 3, pp. 495-503.
European Search Report dated Aug. 5, 2004.
Sergei G. Bavykin et al., "Portable System for Microbial Sample Preparation and Olignucleotide Microarray Analysis", Applied and Environmental Microbiology, vol. 67, No. 2, Feb. 2001, pp. 922-928.
M. Uyttendaele et al., "Influence of bacterial age and pH of lysis buffer on type of nucleic acid isolated", Journal of Microbiological Methods, vol. 26 (1996), pp. 133-138.
R. Boom et al., "Rapid and Simple Method for Purification of Nucleic Acids", Journal of Clinical Microbiology, Mar. 1990, vol. 28, No. 3, pp. 495-503.

* cited by examiner

*Primary Examiner*—Stephen Kapushoc
(74) *Attorney, Agent, or Firm*—Stites & Harbison PLLC; Juan Carlos A. Marquez, Esq.

(57) ABSTRACT

Disclosure is a method of separately recovering deoxyribonucleic acid and ribonucleic acid from a biological sample solution. They are separated and recovered from a single biological sample by controlling pH values, temperature, and/or concentration of cationic ions of a nucleic acid sample solution containing a caotropic agent. It is possible to easily and safely separate and recover deoxyribonucleic acid and ribonucleic acid from the single biological sample.

9 Claims, 6 Drawing Sheets

FIG. 2 (A)
FIG. 2 (B)
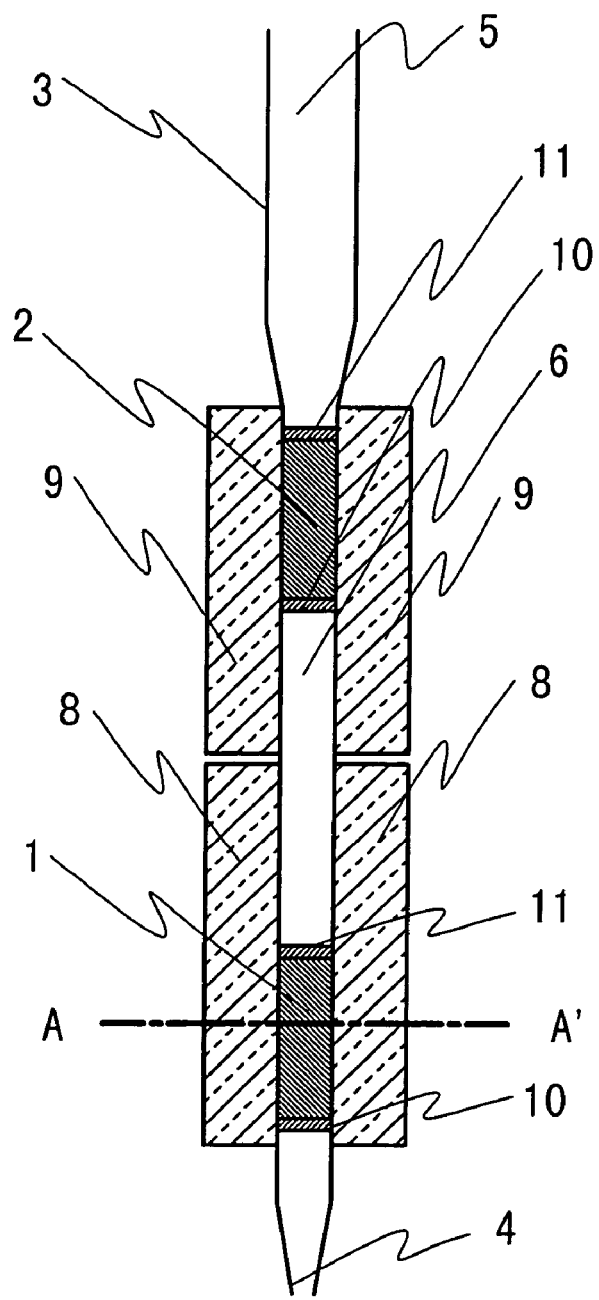
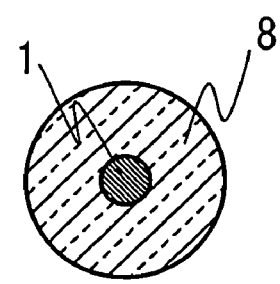
A-A' CROSS-SECTION

A-A' CROSS-SECTION

METHOD OF RECOVERING NUCLEIC ACIDS AND KIT FOR RECOVERING NUCLEIC ACIDS

The present application claims priority from Japanese application JP 2003-139751, filed on May 19, 2003, the content of which is incorporated by reference into this application.

FIELD OF THE INVENTION

The present invention relates to a method of separating and isolating deoxyribonucleic acid and ribonucleic acid from biological samples such as cells or tissues, etc. using a nucleic acid bonding carrier, and to a kit therefor.

BACKGROUND OF THE INVENTION

With a progress of molecular biological analysis technology, it has become possible to acquire very useful information in the fields of clinical diagnosis, genetic engineering, etc by analyzing nucleic acid molecules that carry genetic information. In carrying out the analysis of the nucleic acid molecules, extraction and recovery of nucleic acid molecules are important steps. Generally, ribonucleic acid (RNA) and deoxyribonucleic acid (DNA) present as nucleic acid molecules in a biological sample; it is preferable to separate and recover the deoxyribonucleic acid and ribonucleic acid from a single sample, particularly if an available amount of the sample is limited.

In general, when extracting ribonucleic acid (RNA) and deoxyribonucleic acid (DNA) in the biological sample such as blood, cells, tissue, etc, it is necessary to break cells and isolate nucleic acids by physical treatment with stirring, ultrasonic vibration or heating or by chemical treatment with a surfactant or protease, etc. Then, in order to recover isolated nucleic acids, a cesium chloride density gradient ultra-centrifugal separation, a phenol extraction or column chromatography separation is conducted. These methods are used singly or in combination in accordance with objective nucleic acids, samples used, or usage of nucleic acids to be extracted.

Boom et al proposed a simple method of extracting and recovering nucleic acids from a biological sample, wherein silica particles are used as a nucleic acid bonding carrier in the presence of caotropic salt (See Non-Patent Document 1, for example). According to this method, single strand nucleic acids (single strand DNA and RNA) and double strand nucleic acids (double strand DNA) are separated simultaneously. However, it is difficult to separately recover the isolated deoxyribonucleic acid and ribonucleic acid.

On the other hand, there is a method for selectively recovering ribonucleic acid from a biological sample (See Patent Document 1, for example). According to this method, an acidic solution containing a caotropic agent, a water-soluble organic solvent and a nucleic acid bonding carrier are added to a sample containing ribonucleic acid, followed by mixing the solutions. The carrier to which ribonucleic acid is bound is separated from a liquid phase, thereby to extract and recover only ribonucleic acid by eluting a composite of the ribonucleic acid and carrier composite. However, the deoxyribonucleic acid that coexists with the recovered ribonucleic acid is not recovered.

Further, a method of separating and recovering a double strand/single strand nucleic acid from the same biological sample is disclosed in Patent Document 2, for example. In this method, the double strand nucleic acid in a sample solution is bound to silica particles under proper conditions of a caotropic agent, a chelating agent, pH value, etc. Then, a concentration of the chelating agent in a supernatant from which the silica particles bound to the double strand nucleic acid are removed is changed to thereby cause binding of the single strand nucleic acid to the silica particles. As a result, the double strand nucleic acid/single strand nucleic acids are separately recovered. However, this process needs a centrifugal separation to recover the silica particles, thereby to make the method complicated.

A method of separating double strand nucleic acids and single strand nucleic acids is disclosed in Patent Document 3, for example. In this method, only the deoxyribonucleic acid, i.e. the double strand nucleic acid is bound to an inorganic carrier under a condition free from substances containing alcohol radicals to separate them from the ribonucleic acid. This method may include a step for separating the double strand nucleic acids and the single strand nucleic acids by separate elution from an inorganic carrier, after the double strand nucleic acids/single strand nucleic acids are simultaneously bound to the inorganic carrier.

However, in order to recover the double strand nucleic acids and the single strand nucleic acids, an alcoholic solution of high concentration is needed. Thus, there are problems of safety in handling and of inhibition of enzyme reaction due to alcohol remaining in the recovered product.

Patent Document 1: Japanese Patent Laid-open Hei 11-196869

Patent Document 2: Japanese Patent Re-publication 2000-505295

Patent Document 3: Japanese Patent Laid-open 2002-18797

Non-Patent Document 1: J. Clin. Microbiol. 28; 495-503 (1990)

In extraction of nucleic acids by density gradient ultracentrifugation, a nucleic acid purification processing needs a long period of time. In phenol extraction, care for safe processing must be taken because phenol i.e. a poisonous substance is used. Further, it is unavoidable to make the process complicated.

As for the above-mentioned simplified method for extracting and recovering nucleic acids, it is difficult to separate and recover ribonucleic acid and deoxyribonucleic acid using reagents that are easy to handle, as described above.

BRIEF DESCRIPTION OF DRAWINGS

FIG. 2 is a drawing showing a vessel and device having a mechanism that is capable of controlling a temperature of the positions where the solid carriers are disposed in the vessel.

SUMMARY OF THE INVENTION

Figure 1:
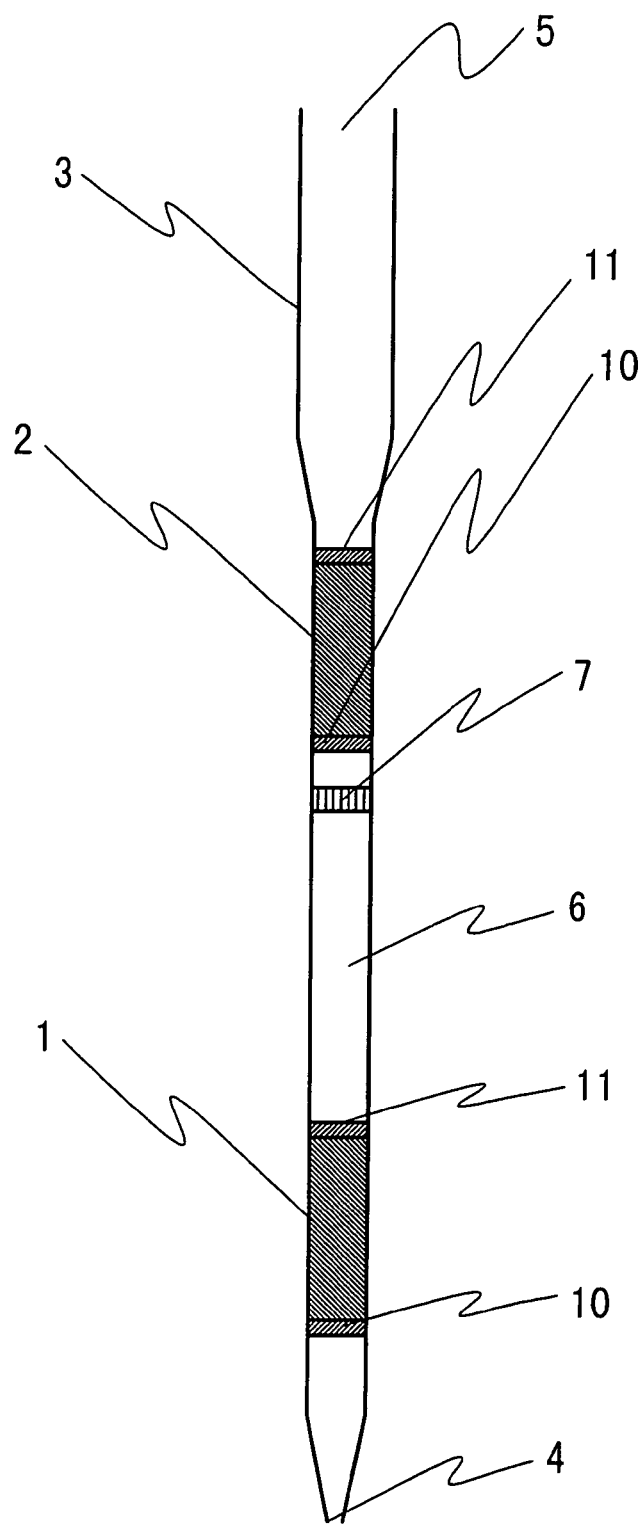
FIG. 1 is a drawing showing a structure of a nucleic acid recovery vessel for supporting two or more solid carriers for deoxyribonucleic acid and ribonucleic acid binding in the same vessel.

An object of the present invention is to safely, simply and separately recover deoxyribonucleic acid molecules and ribonucleic acid molecules present in a biological sample whose cells and tissues are dissolved.

DETAILED DESCRIPTION OF THE EMBODIMENTS

The present invention attains separation and recovery of each of a double strand and ribonucleic acid from a single biological sample, by changing any one of a pH value, temperature, cationic ion concentration of a nucleic acid sample solution containing a caotropic agent.

That is, the method of the invention comprises the following steps.

1) One or more of the pH value, temperature, cationic ion concentration of the sample solution containing deoxyribonucleic acid and ribonucleic acid a condition that the deoxyribonucleic acid is selectively bound to the nucleic acid binding solid carrier. The bound to deoxyribonucleic acid is washed if necessary, eluted with water or desired buffer solution to recover the deoxyribonucleic acid.

2) One or more of the pH value, temperature, cationic ion concentration of the sample solution containing ribonucleic acid which is not bound to the solid carrier are adjusted so as to make a condition that the ribonucleic acid is selectively bound to a newly prepared solid carrier or a solid carrier which is disposed at position different from that of the solid carrier that bound to the deoxyribonucleic acid. The bound ribonucleic acid is washed if necessary, eluted with water or desired buffer solution to recover the ribonucleic acid.

As an example, the present invention is featured by comprising a first step for selectively recovering deoxyribonucleic acid by binding from a sample solution containing deoxyribonucleic acid and ribonucleic acid, and a second step for selectively recovering the ribonucleic acid after the first step, wherein the first and second steps are carried out by changing at least one of a pH value, temperature and cationic ion concentration of the sample solution. The binding is a step for binding nucleic acids to the solid carrier by contacting the sample solution with the solid carrier. The deoxyribonucleic acid is bound to the solid carrier and eluted from the carrier in the first step, and then the ribonucleic acid is selectively bound to the same solid carrier in the second step. Different solid carriers can be used for the respective steps, however.

In the first step, the pH value can be adjusted to 6.0 or more; in the second step, the pH value can be adjusted to 6.0 or less. In the first step, the concentration of bivalent cationic ions is adjusted to 100 to 250 mM, and in the second step, the concentration can be adjusted to 100 mM or less. In the first step, the temperature of the sample solution can be controlled to 50° C. or higher but 100° C. or lower; but, in the second step, the temperature can be controlled to 50° C. or lower.

In another aspect of the present invention, a kit for selectively separating deoxyribonucleic acid and ribonucleic acid comprises a vessel having an opening, a solid carrier to be accommodated in the vessel and a first solution containing 100 mM or more but 250 mM or less of bivalent cationic ions and having a pH value of 6.0 or more, and a second solution containing 100 mM or less of bivalent cationic ions and having a pH value of 6.0 or less, wherein the first solution is used mainly for recovering deoxyribonucleic acid and the second solution is used mainly for recovering ribonucleic acid.

Further, in another aspect of the present invention, in place of the first and the second solutions, the kit comprises a first adjusting solution for adjusting the bivalent cationic ion concentration in the sample solution to 100 mM or more but 250 mM or less, and the pH value to 6.0 or more, and a second adjusting solution for adjust the bivalent cationic ion concentration of the sample solution to 100 mM or less and the pH value to 6.0 or less. The first adjusting solution is used mainly for recovering deoxyribonucleic acid and the second adjusting solution is mainly used for recovering ribonucleic acid.

According to these means, separation and recovery of deoxyribonucleic acid and ribonucleic acid from a single biological sample are realized.

EMBODIMENTS

In the present invention, the biological samples containing deoxyribonucleic acid and ribonucleic acid are ones such as blood, sperm, spit, tissues and cells (bacterial cells, plant cells, animal cells, for example).

Figure 8:
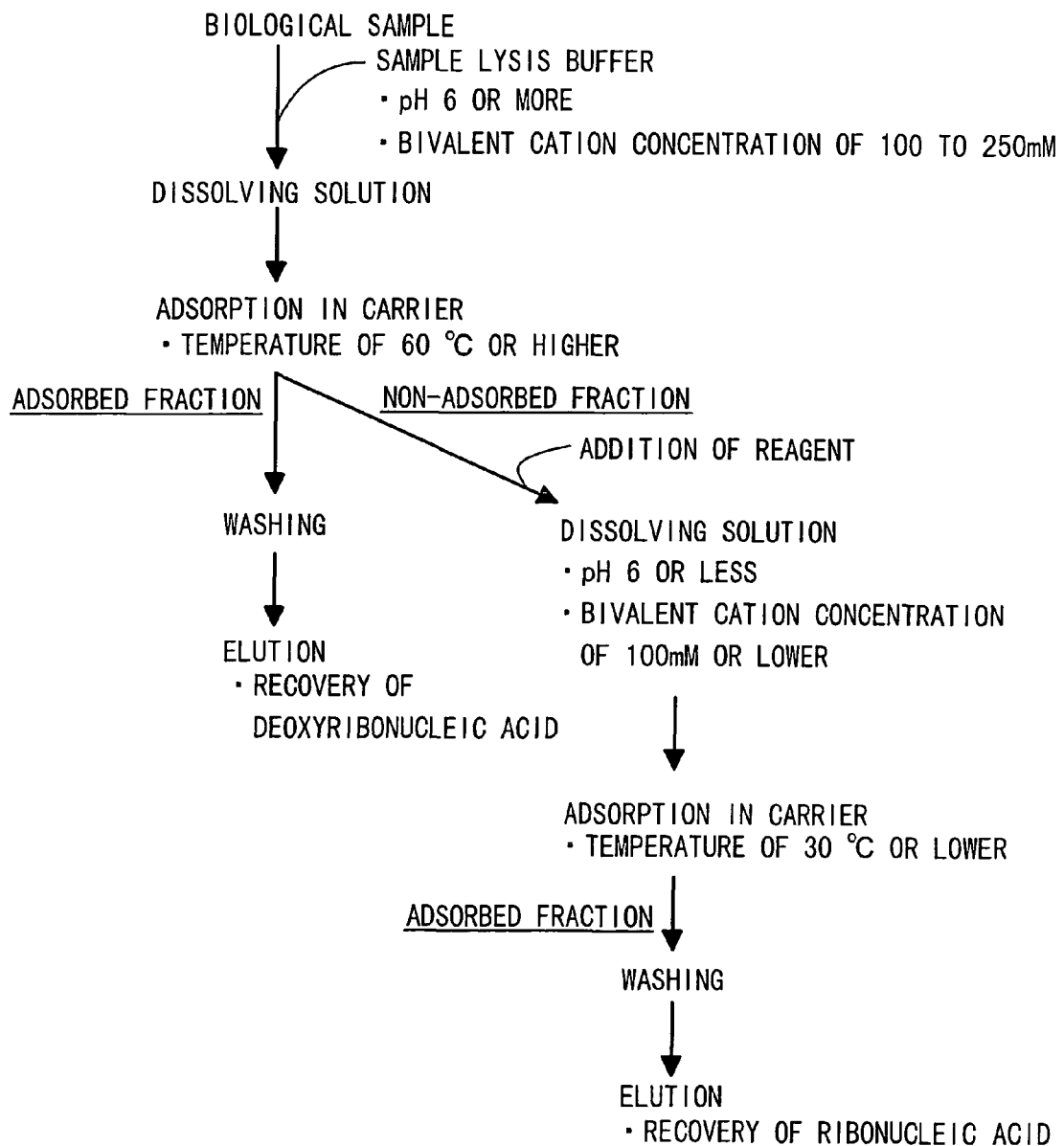
FIG. 8 is a diagrammatic drawing of a method of separating and recovering deoxyribonucleic acid and ribonucleic acid.

A diagrammatic flow chart for isolating and recovering nucleic acids of the present invention is shown in FIG. 8. In the beginning, a biological sample containing deoxyribonucleic acid and ribonucleic acid is dissolved in the presence of a caotropic agent to release the nucleic acids. The lysis buffer containing the caotropic agent is so adjusted as to have a pH value of 6.0 or more and/or to contain 100 mM or more of the bivalent cationic ions. It is preferable to add a buffer agent to the solution. The buffer agent may be contained in the solution containing the caotropic agent in advance, or it can be added after the biological sample is dissolved. Any buffer agents that have been used can be used; especially, buffer agents, which have buffering ability at a pH value of 6.0 or more are preferable. For example, MES (2-morpholino ethanesulfonic acid) buffer is an example; a preferable range of a concentration of the buffer agent is 1 to 500 mM.

The bivalent cationic ions in the solution containing the caotropic agent in the lysis buffer are not limited particularly; magnesium ions, calcium ions and manganese ions are examples, but magnesium ions are preferable. Its concentration is 100 to 250 mM, and more preferably, 150 mM or more.

Caotropic agents used in the present invention include guanidium isothiocyanate/guanidium isocyanate, guanidium chloride, urea, sodium iodide, etc; these agents are used singly or in combination. Although a concentration of the caotropic agent in the solution depends on kinds of the caotropic agents used, in case of guanidium isothiocyanate/guanidium isocyanate, a preferable range of the concentration is 1 to 6 M.

In the present invention, the biological sample solution containing deoxyribonucleic acid and ribonucleic acid that are isolated in the presence of the caotropic agent is contacted with the first solid carrier having a nucleic acid binding ability in the presence of the bivalent cationic ions under the pH value of 6 or more so as to selectively bind deoxyribonucleic acid to the solid carrier, thereby to separate it from ribonucleic acid.

In binding of the deoxyribonucleic acid to the solid carrier, it is preferable for binding of deoxyribonucleic acid to the first solid carrier to contact the biological sample solution with the first solid carrier under the control of temperatures of the solution for lysing and/or the first solid carrier to 50° C. or higher but 100° C. or lower. The bound deoxyribonucleic acid can be eluted and recovered with water or a buffer solution, etc after washing if necessary.

As the first solid carrier and the second solid carrier, there are silica containing solids, which are known as materials having nucleic acid binding ability in the presence of the caotropic agent. Examples are such as glass, the solid carrier contains silica, which is one of materials selected from the group consisting of glass, diatomaceous earth and materials obtained by chemically surface-treating the glass and diatomaceous earth. The structure of the solid carrier is not particularly limited; particles, fibers, filters, etc are acceptable.

In the present invention, ribonucleic acid that is not bound to in the first solid carrier under the predetermined conditions of pH values, bivalent cationic ion concentration and/or temperatures is recovered in the biological sample solution after deoxyribonucleic acid is bound to the first solid carrier. It is preferable to cause binding of this ribonucleic acid to the second solid carrier by adjusting the pH value to 6 or less and/or bivalent cationic ion concentration to 100 mM or less, preferably 50 mM or less. At this step, a temperature of the sample solution and/or the second solid carrier is controlled to 50° C. or lower, preferably 30° C. or lower, followed by contacting the biological sample solution with the second solid carrier. This is suitable for binding of ribonucleic acid to the second solid carrier. The bound ribonucleic acid is eluted and recovered with water or a desired buffer solution after it is washed if desired.

In the present invention, it is necessary to change the pH value from 6 or more to 6 or less, when the first step where deoxyribonucleic acid is bound to the first solid carrier is switched to the second step where the ribonucleic acid is bound to the solid carrier. The pH value of the biological sample solution is changed as desired by 1) adding a solution containing the caotropic agent, the pH value of which is adjusted to 6 or less to the sample solution, or 2) adding a buffer solution or buffer agent having a pH value of 6 or less to the sample solution.

In the present invention, it is necessary to control the concentration of the bivalent cationic ions from 100 mM or more but 250 mM or less, preferably 150 mM or more but 250 mM or less, in the second step, the concentration of bivalent cationic ions is 0 mM or more but 100 mM or less, preferably 0 to 50 mM, when the first step where deoxyribonucleic acid is bound to the solid carrier switched to the second step where ribonucleic acid is bound to the solid carrier. The concentration of the bivalent cationic ions is controlled by 1) adding a solution containing the caotropic agent adjusted by dilution to have the concentration of 100 mM or less, preferably 50 mM or less, or 2) mixing the caotropic solution with the biological sample solution to adjust the concentration to 100 mM or less, preferably 50 mM or less. Addition of a chelating agent for the bivalent cationic ions such as an ethylenediamine tetra-acetic acid (EDTA) solution to the biological sample solution changes the concentration as desired.

Figure 7:
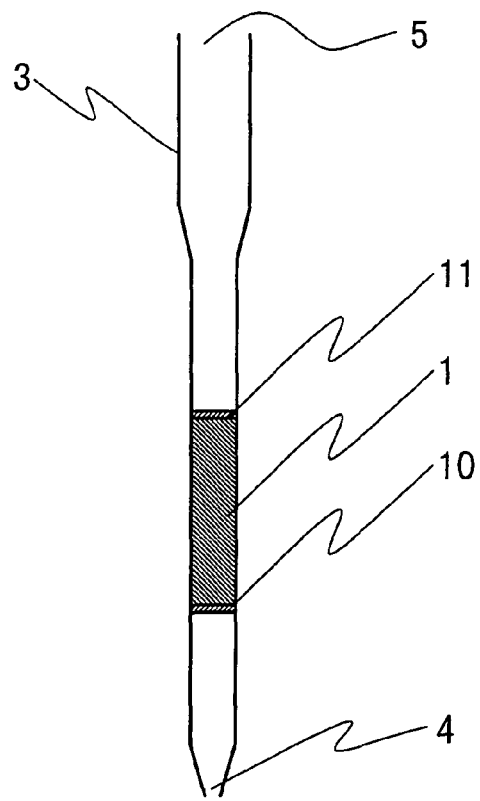
FIG. 7 is a drawing showing a structure and device for recovering nucleic acid that supports bound deoxyribonucleic acid and ribonucleic acid.

In the present invention, the solid carriers used in the first step and second step can be prepared differently for bound deoxyribonucleic acid and ribonucleic acid. FIG. 7 shows an example of the vessel, which supports the solid carrier therein. FIG. 7 shows that the solid carrier 1 is held by nucleic acid binding solid carrier support members 10, 11 in the vessel 3. An opening 5 of the vessel 3 is connected to a syringe pump etc (not shown); the biological sample solution that is so prepared that deoxyribonucleic acid is selectively bound to the solid carrier 1 is introduced from the opening 5 of the vessel 3 into the vessel 3 to bring it into contact with the solid carrier 1. At this time, the temperature of the biological sample solution and the solid carrier 1 is controlled to 60° C. or higher.

The biological sample solution introduced into the vessel 3 is repeatedly subjected to aspiration and ejection to increase the chances of contact between deoxyribonucleic acid and the solid carrier 1, thereby increasing an amount of binding.

Then, the biological sample solution from which deoxyribonucleic acid is removed by contacting the sample solution with the solid carrier 1 containing mainly ribonucleic acid is recovered. Reagents are added to the solution to adjust the pH value of the sample solution and/or the concentration of bivalent cationic ions, thereby to make conditions appropriate for binding of ribonucleic acid. The second step for binding of ribonucleic acid to the solid carrier is carried out by the similar manner as in the first step, using a newly prepared solid carrier. In this step, the temperatures of the biological sample solution and first solid carrier are controlled to 30° C. or lower.

Deoxyribonucleic acid and ribonucleic acid bound to different solid carriers respectively are washed and recovered differently by subjecting to the eluting process. It is possible to use the solid carrier 1 at both first and second steps. In this case, after the first step, washing and eluting suitable for deoxyribonucleic acid are carried out to recover deoxyribonucleic acid from the solid carrier; thereafter, the solid carrier 1 is used at the second step again to bound ribonucleic acid. After the second step, washing and eluting suitable for ribonucleic acid are carried out to recover ribonucleic acid from the solid carrier 1.

Solid carriers, which bind deoxyribonucleic acid and ribonucleic acid, respectively, used in the first step and the second step are prepared separately as another example of solid carrier. As a further example of the solid carrier, there is a vessel wherein two or more of solid carriers for binding deoxyribonucleic acid and ribonucleic acid in the first and second steps are accommodated. FIG. 1 shows one example of the solid carrier, and its operation is explained. In FIG. 1, the solid carrier 1 used in the first step and the solid carrier 2 used in the second step are disposed in the vessel 3 at positions remote from each other.

The opening 4 of the vessel 3 is connected to the syringe (not shown) for aspiration and ejection. Conditions of the prepared biological sample solution are so adjusted as to bind deoxyribonucleic acid to the solid carrier. The biological sample solution is introduced into the vessel 3 to bring it in contact with the first solid carrier 1. The biological sample solution is located between the space 6 in the vessel and the solid carrier 1 so that the biological sample solution contacts with the solid carrier 1, but does not contact with the solid carrier 2.

Further, concussion of the sample solution by reciprocal movement in the vessel is effective to increase chances of contact between the sample solution and the solid carrier, thereby to increase a binding amount.

Deoxyribonucleic acid is removed by contacting with the solid carrier; then, the biological sample solution that contains mainly ribonucleic acid is located in the space 6 of the vessel 3. The sample solution is contacted, mixed with the reagent 7 located in the space 6 of the vessel to dissolve it, whereby the pH value and/or the concentration of bivalent cationic ions are adjusted to such conditions as to bind ribonucleic acid to the solid carrier 2.

Then, the biological sample solution is contacted with the solid carrier 2, is subjected to concussion to bind ribonucleic acid in the solution to the solid carrier 2. After completing the second step, the biological sample solution is discharged from the opening 4 of the vessel 3. The vessel 3 can be divided into two sections each maintaining either the solid carrier 1 or the solid carrier 2. If the vessel 3 is divided, deoxyribonucleic acid or ribonucleic acid bound to the respective solid carriers can be recovered separately by washing and eluting them separately.

In the present invention, when the temperature of the nucleic acid sample solution and/or the solid carrier is controlled to 50° C. or higher, but 70° C. or lower, preferably 50° C. or higher, but 100° C. or lower in the first step; and when the temperature of the nucleic acid sample solution and/or solid carrier is controlled to 0° C. or higher, but 60 or lower, preferably 0° C. or higher, but 30° C. or lower in the second step, deoxyribonucleic acid and ribonucleic acid are recovered separately from the single sample.

FIG. 2(A) shows a side plan view of the vessel and device of one embodiment that is provided with a mechanism for controlling the temperature of positions where the solid carriers are disposed in the vessel, and FIG. 2(B) shows a cross sectional view along the line A-A' of FIG. 2(A). As shown in FIGS. 2(A) and 2(B), temperature control units 8, 9 are disposed near the solid carriers 1, 2 in the vessel 3 in such a manner that the units 8, 9 are in contact with the side face of the vessel 3. The temperature control units 8, 9 controls independently.

In order to carry out the first step, the temperature of the control unit 8 disposed near the solid carrier 1 is controlled to adjust the temperature of the first solid carrier to 50° C. or higher but 100° C. or lower, preferably 70° C.

On the other hand, the temperature in the vicinity of the control unit 9 disposed near the solid carrier 2 is controlled to 0° C. or higher but 60° C. or lower, preferably 30° C. Then, the biological sample solution is placed in the space 6 in such a manner that it contacts the solid carrier 1, but does not touch the solid carrier 2. Further, concussion of the sample solution in the vessel is effective for increasing the amount of binding, because chances of contact between deoxyribonucleic acid and the solid carrier 1 increase.

Next, the biological sample solution is transferred to a vessel so as to bring it contact with the solid carrier 1, but not bring it with the solid carrier 2. After completion of the second step, the biological sample solution is discharged from the opening 4 of the vessel 3. The vessel 3 can be so divided as to accommodate the solid carriers 1, 2, separately. In dividing the vessel, the vessel is divided in such a manner that the solid carriers are supported in the respective divided vessels. Bound deoxyribonucleic acid and ribonucleic acid are recovered from the single sample separately by washing and eluting steps in accordance with kinds of nucleic acids.

Figure 3:
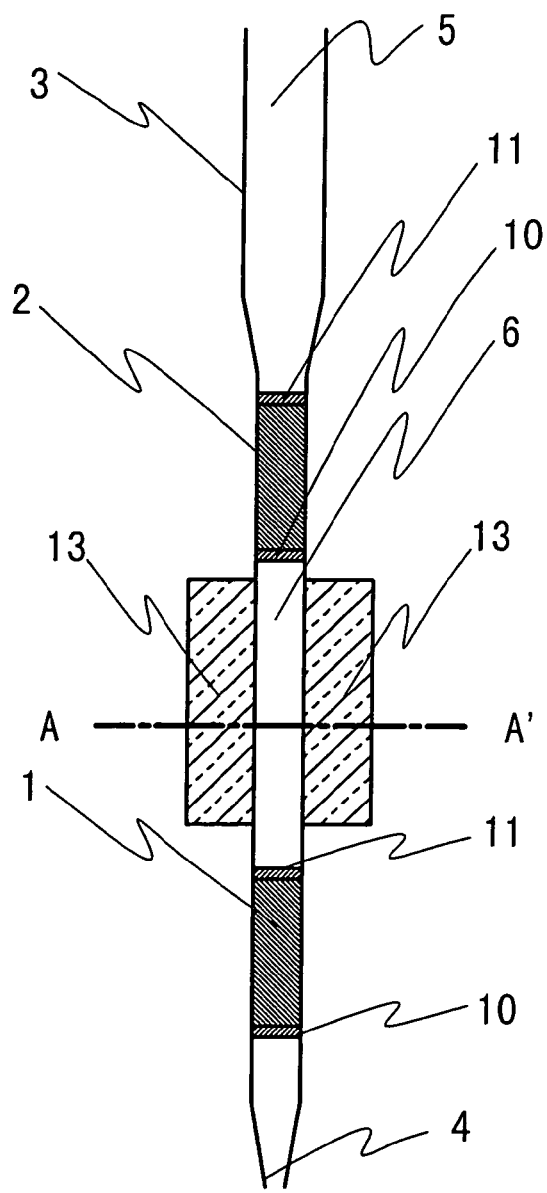
FIG. 3 is a drawing showing a structure of a vessel and device having a mechanism that is capable of controlling the temperature of the portions of the vessel where a plurality of solid carriers are disposed in the vessel.
Figure 3:
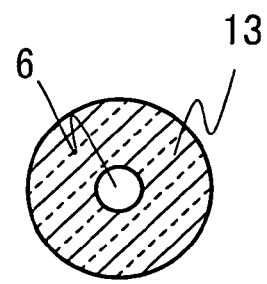

FIG. 3(A) shows a side plan view of a vessel and a device provided with a mechanism capable of controlling temperature of the vessel portion between the solid carriers in the vessel, in place of the embodiment wherein the temperature of the positions of the solid carriers is controlled. FIG. 3(B) shows a cross sectional view of the vessel and device along the line A-A' of FIG. 3(A).

As shown in FIG. 3(A) and FIG. 3(B), a temperature control unit 12 is installed in a space 6, which is close to the solid carriers 1, 2 and is sandwiched by the solid carriers. In order to carry out the first step, the temperature of the biological sample solution is controlled to 50° C. or higher but 100° C. or lower, preferably 70° C. in advance. Then, the biological sample solution is introduced into the vessel 3 through the opening 4 so that the solution is located between the space 6 and the solid carrier 1 where the solution touches the solid carrier 1 but does not touch the solid carrier 2. Concussion of the liquid in the vessel at the position increases chances of contact between deoxyribonucleic acid and the solid carrier 1, thereby to increase an amount of binding.

Then, the solution that is freed from deoxyribonucleic acid by contact with the solid carrier 1, but mainly contains ribonucleic acid is supported in the space 6 of the vessel. The temperature control unit 13 installed near the space 6 controls a temperature of the sample solution to 0° C. or higher but 60° C. or lower, preferably 30° C. Thereafter, the solution containing ribonucleic acid mainly is contacted with the solid carrier 2 to bind ribonucleic acid.

After completion of the second step, the biological sample solution is discharged from the opening 4 of the vessel 3. The vessel 3 can be divided at the space so that the solid carriers 1, 2 are separately supported. In dividing the vessel, it is possible to place each of the solid carriers in each of the divided vessels. The deoxyribonucleic acid and ribonucleic acid are separately recovered from the single sample by washing and eluting from the respective solid carriers supported in the respective divided vessels.

In the following, the advantages of the present invention will be explained by showing embodiments of the invention.

Embodiment 1

Effect of pH Value on Binding of Deoxyribonucleic Acid and Ribonucleic Acid in Solid Carrier Materials and Processes Are as Follows.

1. Preparation of Nucleic Acid Sample

An Arabidopsis green plant after one week of planting was frozen in liquid nitrogen, and then ground to fine powder in liquid nitrogen. 5 mL of TRIZOL reagent (manufactured by Invitrogen) per 0.5 g of frozen plant tissue was added; the total RNA was prepared in accordance with the manufacturer's protocol. As a DNA sample, DNA fragments prepared in the following method were used. The PCR-amplified cDNA fragments using M13 forward and reverse primers were used. Two fragments of Arabidopsis cDNA cloned into *E. Coli.* vector pSPORT manufactured by Invitrogen) having about 2 kb were used, as a template fro PCR amplification.

2. Solid Carrier

As a solid carrier for binding of nucleic acid, 5 mg of Quartz Glass Wools; B grade (manufactured by Toshiba Ceramics) was used wherein the wool was disposed at the tip of the capillary chip.

3. Nucleic Acid Binding Solution 29.54 g of Guanidinium isothiocyanate (manufactured by Invitrogen) was dissolved in 100 mM of MES-KOH solutions of various pH values to prepare the final concentration of 5 M. Since the pH value may change by dissolving guanidinium isothiocyanate, the final pH value was determined after dissolving guanidinium isothiocyanate.

4. A Binding Method of Nucleic Acids to the Solid Carrier

10 μL of the total RNA sample (equivalent to 3 μg) and 110 μL of sterilized water were added to 480 μL of the guanidium isothiocyanate solution, followed by stirring and mixing. The mixed solution was contacted with the Quartz Glass Wools disposed at the tip of the capillary chip. The mixed nucleic solution was reciprocally shaken 20 times in the capillary chip by means of the syringe to effect binding of nucleic acids to the solid carrier. In case of DNA, a 10 μL DNA sample (equivalent to 0.5 μg) was used to effect binding to the similar manner.

5. Determination of Binding to the Solid Carrier

The binding to the solid carrier was analyzed by determining an amount of nucleic acid remaining in the mixed solution after contacting the solution with the solid carrier. 60 μL of a sodium acetate solution of 5 M was added to 600 μL of the non-bound fraction, and 1.2 mL of ethanol was added to the mixture. Then, the solution was stood for 30 minutes at—80° C., then, centrifuged to precipitate the nucleic acid. After the precipitate was washed with 80% ethanol, it was dried. 10 μL of fertilized water was added to the dried precipitate to dissolve the nucleic acids. Then, a sample loading buffer was added to the nucleic acid sample, and the sample was denaturalized. After the sample was cooled on ice, the sample was subjected to electrophoresis using agarose gel containing Formalin. After electrophoresis, the nucleic acids were stained with ethidium bromide to detect them. The intensity of fluorescence of the detected bands was determined with an image analyzer FMBIO (manufactured by TAKARA).

Figure 4:
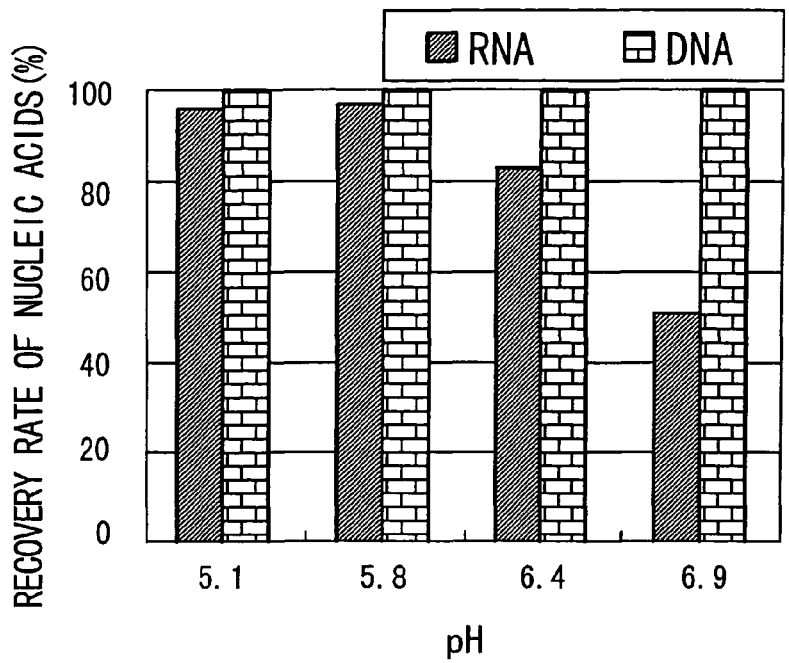
FIG. 4 is a drawing showing an effect of pH values on deoxyribonucleic acid and ribonucleic acid binding to the solid carrier.

Concerning the above material and method, the effect of pH values on binding of deoxyribonucleic acid and ribonucleic acid to the solid carrier was investigated under the condition of 4 M as the final concentration using 5 M guanidium isothiocyanate solutions prepared by adjusting their pH values with 100 mM MES-KOH buffer solutions to 5.1, 5.8, 6.4 and 6.9, respectively. The ratio of the bound amount of nucleic acids to the amount of used nucleic acids in the sample was obtained as a recovery rate (%) of nucleic acid. FIG. 4 shows the result. From FIG. 4, it is apparent that although deoxyribonucleic acid (DNA) showed about 100% recovery rate over the all pH values investigated, ribonucleic acid (RNA) showed a lowered recovery rate at a pH value of 6.4 or more, and the recovery rate at pH value of 6.9 or less became about half. From these results, it has been revealed that binding of ribonucleic acid decreases at pH vale of 6 or more, and deoxyribonucleic acid is preferentially bound to the solid carrier.

Embodiment 2

Effect of Temperature on Binding of Deoxyribonucleic Acid and Ribonucleic Acid

Figure 5:
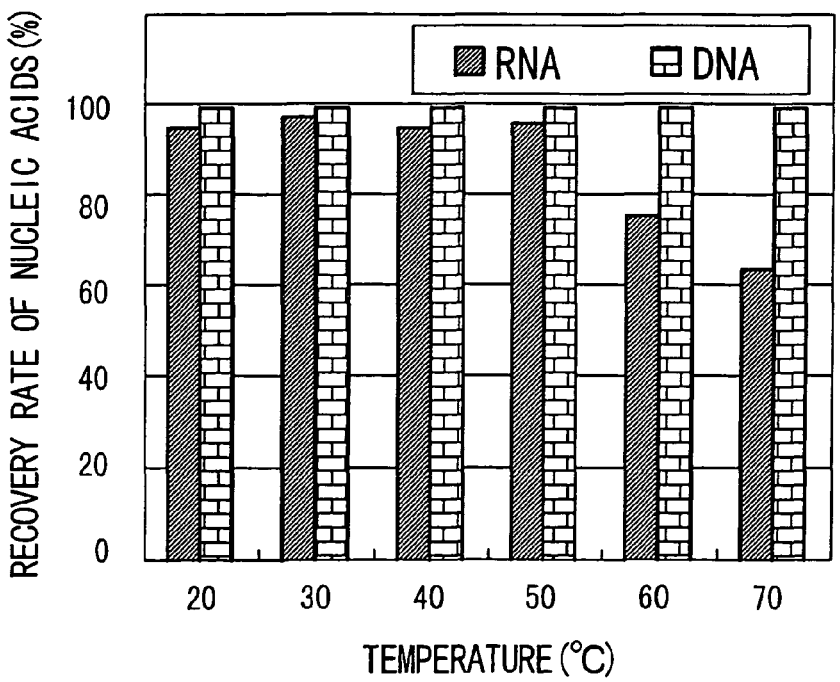
FIG. 5 is a drawing showing an effect of temperature on deoxyribonucleic acid and ribonucleic acid binding to the solid carrier.

Effect of temperature on binding of deoxyribonucleic acid and ribonucleic acid was investigated under the conditions of the final concentration 4 M of guanidium isothiocyanate (pH 5.8). The material and method were the same as those in Embodiment 1. As shown in FIG. 5, although the recovery rates of deoxyribonucleic acid (DNA) by binding showed were 98% or more at any tested temperatures, the recovery rates of ribonucleic acid (RNA) decreased at 60° C. or higher to be about 74%, and at 70° C., the recovery rate was about 65%. From these results, it has been revealed that under the condition of the temperature of 60° C. or higher, binding of ribonucleic acid decreases, but deoxyribonucleic acid is preferentially bound to the solid carrier.

Embodiment 3

Figure 6:
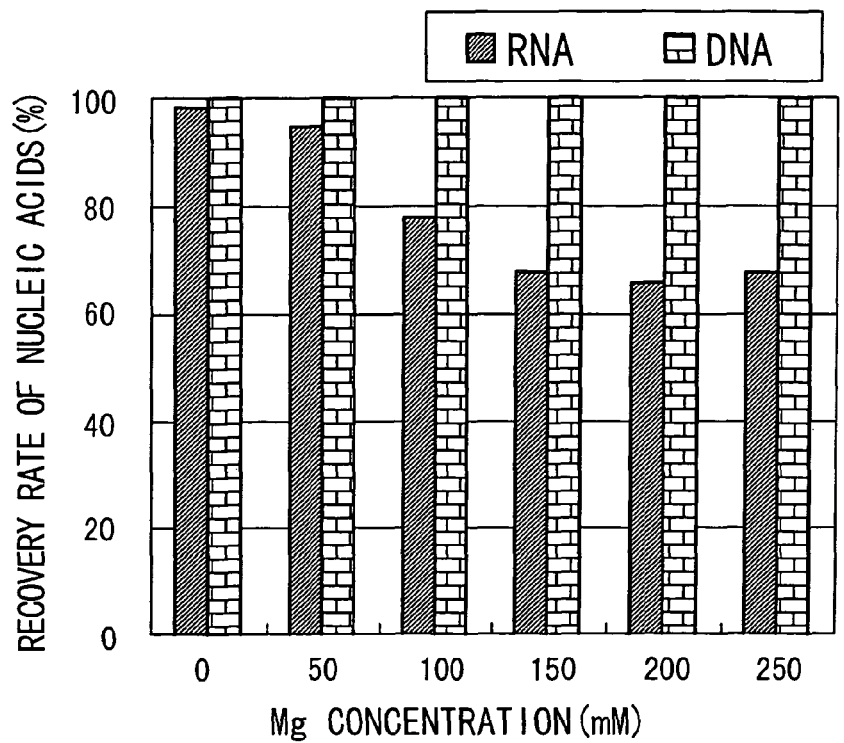
FIG. 6 is a drawing showing an effect of cationic ions on deoxyribonucleic acid and ribonucleic acid binding to the solid carrier.

Effect of Cationic Ions on Binding of Deoxyribonucleic Acid and Ribonucleic Acid in a Solid Carrier The effect of bivalent cationic ions on binding of deoxyribonucleic acid and ribonucleic acid to the solid carrier under the condition of the final concentration of 4 M of guanidium isothiocyanate (pH 5.8) was investigated. The material and method were the same as those of Embodiment 1; the result shown in FIG. 6 is concerned with Mg ions as an example. As shown in FIG. 6, deoxyribonucleic acid (DNA) showed almost 100% recovery rates over any concentrations of Mg ions, while ribonucleic acid (RNA) showed the decreased recovery rate at a concentration of Mg ions of 100 mM or more, and when the concentration is 150 mM or more, the recovery rate decreased to about 68%. From these results, it has been revealed that Mg ions inhibit binding of ribonucleic acid to the solid carrier. Accordingly, when the concentration of Mg ions is 100 mM or more, binding of ribonucleic acid (RNA) decreases, but deoxyribonucleic acid (DNA) is preferentially bound to the solid carrier.

From the above results, binding of ribonucleic acid decreases under the conditions of pH value of 6 or more, a temperature of 60° C. or higher and/or a concentration of cationic ions of 100 mM or more, but, preferential binding of deoxyribonucleic acid to the solid carrier takes place. Further, under the conditions of a pH vale of 6 or less, a temperature of 60° C. or lower and/or a concentration of cationic ions of 100 mM or less, good binding of ribonucleic acid was observed.

Based on these results, it is considered that the pH value for preferential binding of deoxyribonucleic acid to the solid carrier is 6 or more, and the pH value for preferential binding of ribonucleic acid is 6 or less.

Further, it is considered that the temperature for preferential binding of deoxyribonucleic acid is 50° C. or higher but 100° C. or lower, preferably 50° C. or higher but 70° C. or lower; and the temperature for preferential binding of ribonucleic acid to the solid carrier is 0° C. or higher, preferably 0° C. or higher but 30° C. or lower.

In addition, it is considered that the concentration of bivalent cationic ions in the biological sample solution for preferential binding of deoxyribonucleic acid to the solid carrier is 100 mM or more but 250 mM or less, preferably 150 mM or more but 250 mM or less, and the concentration of the bivalent cationic ions for the preferential binding of ribonucleic acid is 0 mM or more but 100 mM or less, preferably 0 mM or more but 50 mM or less.

Embodiment 4

Fractional Binding of Nucleic Acids to the Solid Carriers using a Mixture of Deoxyribonucleic Acid and Ribonucleic Acid The first step for binding-recovering deoxyribonucleic acid and the second step for binding-recovering ribonucleic acid were conducted using a mixture of deoxyribonucleic acid and ribonucleic acid, wherein the pH value, $Mg^{2+}$ concentration and temperature of the guanidium isothiocyanate were changed to investigate recovering rates of the nucleic acids. The guanidium solution containing deoxyribonucleic acid (DNA: PCR fragments of ca. 2 kb, equivalent to 0.3 μg) and ribonucleic acid (total RNA: equivalent to 3 μg) was prepared. The solution had a pH value of 6.5 and a $Mg^{2+}$ concentration of 150 mM. The temperature of the solution was elevated to 60° C., and the temperature was maintained. The solution was contacted with a carrier to conduct the first step to bind deoxyribonucleic acid.

The pH value and $Mg^{2+}$ concentration of the non-bound (1) in the first step were adjusted to 6 or less and 50 mM or less, respectively, by adding a 4 M guanidium isothiocyanate solution (pH value 5.0) to the fraction (1). Then, the temperature of the prepared fraction was cooled down to 30° C. After the temperature reached 30° C., the fraction was contacted with a solid carrier and a solution, which are different from ones used in the first step, to conduct the second step. The remaining nucleic acids were recovered from the non-bound fraction in the first step (1) and the non-bound fraction in the second step (2) by an ethanol precipitation method. The recovered nucleic acids were subjected to electrophoretic analysis to determine a recovery rate of the nucleic acid at each step (Table 1).

Table 1: Recovery rates of deoxyribonucleic acid (DNA) and ribonucleic acid (RNA) in the first step and second step.

TABLE 1

|  | First step | Second step |
| --- | --- | --- |
| DNA recovery rate | 99% or more | Less than 1% |
| RNA recovery rate | 5-10% | 75-80% |

As shown in Table 1, almost all of deoxyribonucleic acid (DNA) was bound and recovered in the first step. On the other hand, the recovery rate of ribonucleic acid (RNA) was about 10% or less of the used ribonucleic acid, while RNA was bound, too. From these facts, deoxyribonucleic acid was preferentially bound to the first step under the conditions of the pH value of 6 or more, 100 mM or more of $Mg^{2+}$ concentration, and the temperature of 60° C. or higher. In the second step, on the other hand, about 75-80% of the used ribonucleic acid (about 90% of ribonucleic acid remaining in the non-bound fraction (1)) was bound and recovered.

From the above results, in the selective binding of deoxyribonucleic acid and ribonucleic acid, binding of ribonucleic acid decreases and preferential binding of deoxyribonucleic acid to the solid carrier is achieved, when the pH value is 6 or more, the temperature is 60° C. or higher and/or the $Mg^{2+}$ concentration is 100 mM or more. When the pH value is 6 or less, the temperature is 60° C. or lower and/or the $Mg^{2+}$ concentration is 100 mM or less, a good binding of ribonucleic acid was achieved.

According to the above embodiment, both of deoxyribonucleic acid and ribonucleic acid can be recovered from an extremely small amount of the sample. For example, DNA and RNA are extracted and recovered from one specific section cut out from the tissue slice by such as laser microdissection method, whereby the analysis of genomic mutation on chromosome DNA and of mRNA expression in the specific section are possible.

According to the present invention, it is possible to separately recover, easily and safely, deoxyribonucleic acid and ribonucleic acid molecules present in a single biological sample. Further, in extracting and recovering DNA and RNA separately from the single sample, it is possible to extract and recover them from an extremely small amount of sample, without preparing a large amount of sample.

What is claimed is:

1. A method of recovering nucleic acids from a sample solution, said method comprising:

contacting a first sample solution comprising ribonucleic acid (RNA) and double stranded deoxyribonucleic acid (DNA) with quartz glass wool in a first binding reaction, wherein the first binding reaction results in binding of said DNA to said quartz glass wool thereby creating a second sample solution comprising the RNA, wherein during the first binding reaction the first sample solution has a pH value of 6.0 or higher but 6.9 or lower, a temperature of 50° C. or higher but 70° C. or lower and a magnesium ion concentration of 100 mM or higher but 250 mM or lower;

contacting the second sample solution with quartz glass wool in a second binding reaction, wherein the second binding reaction results in the RNA binding to said quartz glass wool in the second sample solution, wherein during the second binding reaction the second sample solution has a pH value of 5.1 or higher but 6.0 or lower, a temperature of 20° C. or higher but 50° C. or lower and a magnesium ion concentration of 100 mM or lower; and recovering said DNA bound to the quartz glass wool in the first binding reaction, and recovering the RNA bound to the quartz glass wool in the second binding reaction.

2. The method of recovering nucleic acids according to claim 1, wherein in the first binding reaction said DNA is bound to the quartz glass wool by contacting the first sample solution with the quartz glass wool and said DNA is eluted from the quartz glass wool after the first binding reaction; and in the second binding reaction the RNA is bound by contacting the second sample solution with the quartz glass wool from which said DNA has been eluted.

3. The method of recovering nucleic acids according to claim 1, wherein the deoxyribonucleic acid is bound to a first quartz glass wool by contacting the first sample solution with the first quartz glass wool in the first binding reaction; and the RNA is bound to a second quartz glass wool by contacting the second sample solution with the second quartz glass wool in the second binding reaction.

4. The method of recovering nucleic acids according to claim 1, wherein the pH value of the sample solution is lowered before the second binding reaction.

5. The method of recovering nucleic acids according to claim 1, wherein the magnesium ion concentration of the second sample solution is lowered by diluting the second sample solution before the second binding reaction.

6. The method of recovering nucleic acids according to claim 1, wherein the magnesium ion concentration of the second sample solution is lowered by adding a chelating agent to the second sample solution before the second binding reaction.

7. The method of recovering nucleic acids according to claim 3, wherein a temperature is changed of at least one of the first quartz glass wool, second quartz glass wool and a sample solution.

8. The method of recovering nucleic acids according to claim 3, wherein a temperature change is effected by controlling a temperature of a vessel portion where the first quartz glass wool and/or second quartz glass wool is disposed.

9. The method of recovering nucleic acids according to claim 3, wherein a temperature change is effected by controlling a temperature at a portion between the first quartz glass wool and second quartz glass wool, the portion being in a vessel where the first and second quartz glass wool are disposed.

* * * * *